US007157498B2

(12) United States Patent
Dauban et al.

(10) Patent No.: US 7,157,498 B2
(45) Date of Patent: Jan. 2, 2007

(54) DIAMINES HAVING A CASR MODULATING ACTIVITY

(75) Inventors: Philippe Marcel Dauban, Sanite-Genevieve-des-Bois (FR); Robert Hugh Dodd, Paris (FR); Helene Veronique Faure, Gif-sur-Yvette (FR); Martial Ruat, Bourg la Reine (FR); Pierre Jean-Paul Potier, Paris (FR); Albane Kessler, Paris (FR)

(73) Assignee: Centre National de la Recherche Scientifique (CNRS), Paris Cedex (FR)

( * ) Notice: Subject to any disclaimer, the term of this patent is extended or adjusted under 35 U.S.C. 154(b) by 357 days.

(21) Appl. No.: 10/344,146

(22) PCT Filed: Aug. 7, 2001

(86) PCT No.: PCT/FR01/02562

§ 371 (c)(1),
(2), (4) Date: Jan. 16, 2004

(87) PCT Pub. No.: WO02/12181

PCT Pub. Date: Feb. 14, 2002

(65) Prior Publication Data

US 2005/0192317 A1    Sep. 1, 2005

(30) Foreign Application Priority Data

Aug. 8, 2000   (FR) .................................. 00 10427

(51) Int. Cl.
*A61K 31/18* (2006.01)
*C07C 303/00* (2006.01)
(52) U.S. Cl. ........................................ 514/602; 564/84
(58) Field of Classification Search ................. 564/84; 514/602
See application file for complete search history.

(56) References Cited

U.S. PATENT DOCUMENTS 3,262,977 A    7/1966   Harsanyi et al.

FOREIGN PATENT DOCUMENTS

| WO | WO 93/04373 A  | 3/1993 |
| WO | WO 93/04373 A1 | 3/1993 |
| WO | WO 95/11221 A  | 4/1995 |
| WO | WO 95/11221 A1 | 4/1995 |
| WO | WO 97/37967 A1 | 10/1997 |
| WO | WO 98/44925 A1 | 10/1998 |
| WO | WO 98/45255 A1 | 10/1998 |
| WO | WO 99/51241 A1 | 10/1999 |
| WO | WO 99/51569 A1 | 10/1999 |

OTHER PUBLICATIONS

Antonsen et al., "A calcimimetic agent acutely suppresses parathyroid hormone levels in patients with chronic renal failure", *Kidney International*, 1998, pp. 223-227, vol. 53, The International Society of Nephrology.

Brown, "Cloning and characterization of an extracellular $Ca^{2+}$—sensing receptor from bovine parathyroid", *Nature*, Dec. 9, 1993, pp. 575-580, vol. 366.

Brown, "The extracellular calcium sensing receptor: Its Role in Health and Disease", *Annu. Rev. Med.*, 1998, vol. 49, pp. 15-29, Annual Reviews, Inc.

Chattopadhyay et al., "The Calcium-Sensing Receptor: A Window into the Physiology and Pathophysiology of Mineral Ion Metabolism", *Endocrine Reviews*, 1996, vol. 17, No. 4, pp. 289-307, The Endocrine Society, USA.

Ferry et al., "Effects of divalent Cations and of a Calcimimetic on Adrenocorticotropic Hormone Release in Pituitary Tumor Cells", *Biomedical and Biophysical Research Communication*, 1997, pp. 866-873, vol. 238, No. 3, Academic Press.

Nageli et al., "81, Rhodium(II)-Catalyzed CH Insertions with {[(4-Nitrophenyl)sufonyl]imino}phenyl-$\lambda^3$-iodane," *Helvetica Chimica Acta*, Jun. 30, 1997, pp. 1087-1105, vol. 80, No. 4, Verlag Helvetica Chimica Acta, Bale, CH.

Nemeth et al., "Calcimimetic Compounds: a Direct Approach to Controlling Plasma Levels of Parathyroid Hormone in Hyperparathyroidism", *TEM*, 1999, vol. 10, No. 2, pp. 66-71, Elsevier Science.

(Continued)

*Primary Examiner*—Joseph K. McKane
*Assistant Examiner*—Robert Shiao
(74) *Attorney, Agent, or Firm*—Foley & Lardner LLP

(57) ABSTRACT

The invention concerns diamines of general formula (I), wherein: A represents a group A1 or A2 of general formula (II); B represents a group B1 or B2 of general formula (III); X represents a $SO_2$, $CH_2$, C=O or COO; Y=Z represents a group of formula CH(R25)—CH(R26) or CH(R27)=(R28), and R1 to R28, identical or different, represent independently of one another, a hydrogen or halogen atom or an alkyl, cycloalkyl, CN, $NO_2$, hydroxy, aryl, aralkyl, alkoxy, aryloxy, amino, alkylamino, dialkylamino, cycloalkylamino, arylamino, arylalkylamino, diarylamino diarylalkylamino, trihalogenoalkyl or trihalogenoalkoxy group, provided that in the group A1, at least one of the radicals R1, R2, R3, R4 or R5 represents the hydrogen atom when the other four do not represent the hydrogen atom and in the group B1, at least one of the radicals R13, R14, R15, R16 or R17 represents the hydrogen atom when the other four do not represent the hydrogen atom, and their salts with a pharmaceutically acceptable acid, in the form of racemic mixture or their optically pore isomers. The invention also concerns their preparation, pharmaceutical compositions comprising them and their use as CaSR activity modulator and as medicine particularly designed for the treatment of psychological diseases and disorders involving CaSR activity modulation.

15 Claims, No Drawings

OTHER PUBLICATIONS

Nemeth et al., "Calcimimetics with potent and selective activity on the parathyroid calcium receptor", *Proc. Natl. Acad. Sci.*, Mar. 1998, pp. 4040-4045, vol. 95, Pharmacology, USA.

Pollak et al., "Autosomal dominant hypocalcaemia caused by a $Ca^{2+}$—sensing receptor gene mutation", *Nature Genetics*, Nov. 1994, pp. 303-307, vol. 8.

Pollak et al., "Mutations in the Human $Ca^{2+}$-sensing Receptor Gene Cause Familial Hypocalciuric Hypercalcemia and Neanatal Severe Hyperparathyroidism", *Cell*, Dec. 31, 1993, pp. 1297-1303, vol. 75, Cell Press.

Ruat et al., "Calcium sensing receptor: Molecular cloning in rat and localization to nerve terminals", *Proc. Natl. Acad. Sci.*, Apr. 1995, pp. 3161-3165, vol. 92, Neurobiology, USA.

Ruat et al., "Cloned and Expressed Rat $Ca^{2+}$-sensing Receptor", *The Journal of Biological Chemistry*, Mar. 15, 1996, pp. 5972-5975, vol. 271, No. 11, The American Society for Biochemistry and Molecular Biology, Inc., USA.

Schlichter et al., "Asymmetric Reductive Amination of Cycloalkanones, XIII: Enantioselective Amidoamination: A New Regiospecific Strategy for the Synthesis of Chiral Cyclohexane-1,2-diamino-Derivatives," *Arch. Pharm.*, 1993, vol. 326, No. 7, pp. 429-436, VCH Verlagsgesellschaft, Weinheim, DE.

Schlichter et al., "Novel,Enantioselective Synthesis of Vicinal Cyclohexane-Diamines as Key-Intermediates for Highly Selective Opioid Kappa and Sigma Agonists," *Tetrahedron: Asymmetry*, 1992, pp. 3289-3333, vol. 3, No. 3, Elsevier Science Publishers, Amsterdam, NL.

Silverberg et al., "Short term inhibition of parathyroid hormone secretion by a calcium receptor agonist in patients with primary hyperparathyroidism", *New England Journal of Medicine*, Nov. 20, 1997, pp. 1506-1510, vol. 337, No. 21.

Sodergren et al., "Preparation and Evaluation of Nitrene Precursors ($PhI=NSO_2Ar$) for the Copper-Catalyzed Aziridination of Olefins," *Tetrahedron Letters*, Sep. 29, 1997, pp. 6897-6900, vol. 38, No. 39, Elsevier Science Publishers, Amsterdam, NL.

Wada et al., "NPS R-568 halts or reverses osteitis fibrosa in uremic rats", *Kidney International*, 1998, pp. 448-453, vol. 53, The International Society of Nephrology.

Wada et al., "The calcimimetic Compound NPS R-568 suppresses Parathyroid Cell Proliferation in Rats with Renal Insufficiency", *J. Clin. Invest.*, pp. 2977-2983, vol. 100, No. 12, The American Society for Clinical Investigation, Inc.

Ye et al., "Amyloid-B Proteins Activate $Ca^{2+}$—Permeable Channels Through Calcium-Sensing Receptors", *Journal of Neuroscience Research*, 1997, pp. 547-554, vol. 47, Wiley-Liss, Inc.

W. H. Schlichter et al.; "Novel enantioselective synthesis of vicinal cyclohexanediamines as key-intermediates for highly selective opioid kappa and sigma agonists", Tetrahedron: Asymmetry, vol. 3, No. 3, 1992, pp. 329-333, Elsevier Science Publishers, Amsterdan, NL.

W. H. Schlichter et al., "Asymmetric reductive animation of cycloakanones, XIII. Enantioselective amidoamination: a new regiospecific strategy for the synthesis of chiral cyclohexane-1,2-diamino-derivatives", Archive Der Pharmazie, vol. 326, No. 7, 1993, pp. 429-436, VCH Verlagsgesellschaft, Weinheim, DE.

DIAMINES HAVING A CASR MODULATING ACTIVITY

The present invention relates to compounds having extracellular calcium ($(Ca^{2+})_e$) and extracellular magnesium ($(Mg^{2+})_e$) ion receptor or Calcium Sensing Receptor (CaSR) modulating activity. It relates in particular to a novel class of amine-containing compounds, their preparation, the pharmaceutical compositions containing them and their use as modulator of the activity of CaSRs and as medicament intended in particular for the treatment of physiological diseases or disorders involving the modulation of CaSR activity.

The CaSR modulating activity corresponds to the capacity to produce, induce or antagonize biological responses observed by the variations in the concentration of extracellular calcium ions $(Ca^{2+})_e$ and of extracellular magnesium ions $(Mg^{2+})_e$. This activity may be of the calcimimetic type or of the calcilytic type.

The $(Ca^{2+})$ e and $(Mg^{2+})_e$ ions play an important role in the body because they regulate calcium homeostasis on which depend the vital functions. Thus, hypercalcemia, that is to say states where the $(Ca^{2+})_e$ ions are above the mean threshold, have a major incidence on numerous functions such as cardiac, renal or intestinal functions. They deeply affect the central nervous system (Chattopadhyay et al., Endocr. Review, 1998, vol. 17, p. 289–307).

The CaSRs are proteins which are sensitive to $(Ca^{2+})_e$ and $(Mg^{2+})_e$ ions, and are present in the parathyroid glands, the kidney, the intestine, the lungs, the bone cells, the brain, the spinal cord, sensitive neurons the pituitary gland, the stomach, the keratinocytes (Brown et al., Nature, 1993, vol. 366, p. 575–580; Ruat et al., Proc. Natl. Acad. Sci., USA, 1995, vol. 92, p. 3161–3165; Brown et al., Ann. Rev. Med., 1998, vol. 49, p. 15–29). These proteins are encoded by a single gene isolated from various animal species. They belong to the family of G protein-coupled receptors with seven transmembrane domains, and exhibit structural homologies with the metabotropic glutamate receptors, $GABA_B$ receptors, hypothetical pheromone and taste receptors. Activating or inhibitory mutations of the gene in humans are responsible for extremely serious genetic diseases which cause hypocalcemia or hypercalcemia (Pollack et al., Cell, 1993, vol. 75, p. 1297–1303; Pollack et al., Nature Genetics, 1994, vol. 8, p. 303–307; Brown et al., Ann. Rev. Med., 1998, vol. 49, p. 15–29). The functions linked to the expression of these proteins in the tissues are not yet all known and are the subject of a very high research activity, particularly as regards the CaSRs present in the parathyroid and thyroid glands, the kidney, the intestine, the spinal cord, the brain and the bone cells.

In the parathyroid gland, the CaSRs modulate the secretion of the parathyroid hormone (PTH) which is the main regulator of calcium homeostasis: the increase in $(Ca^{2+})_e$ ions in the serum will activate the CaSRs present on the cells of the thyroid gland and reduce the secretion of the PTH hormone.

Complementary DNA encoding rat CaSR has been isolated from a rat striatum cDNA library (Ruat et al., Proc. Natl. Acad. Sci., 1995, vol. 92, p. 3161–3165). This receptor is identical with respect to its amino acid sequence to that expressed in the other tissues. Transfected Chinese hamster ovary_(CHO) cells expressing rat CaSR(CHO(CaSR)) have been characterized and the chemical signals (second messengers) induced by the activation of this receptor have been analyzed. Thus, a biochemical test which makes it possible to measure the accumulation of tritiated inositol phosphates [$^3$H]IP in response to the activation of the receptor has been developed (Ruat et al., J. Biol. Chem., 1996, vol. 271, p. 5972–5975; Ferry et al., Biochem. Biophys. Res. Commun., 1997, vol. 238, p. 866–873).

It has been shown that the $Ca^{2+}$, $Mg^{2+}$, but also $Ba^{2+}$ ions in millimolar concentration ranges stimulate the CaSRs. The activation of the CaSRs could be induced in the brain by the β-amyloid peptides which are involved in neurodegenerative diseases such as Alzheimer's disease (Ye et al., J. Neurosci. Res., 1997, vol. 47, p. 547–554).

Disruption of the CaSR activity is associated with biological disorders such as osteoporosis, Paget's disease, rheumatoid arthritis, tumors associated with humoral hypercalcemia, osteoarthritis, osteosarcomas, fractures, primary and secondary hyperparathyroidism, osteoporosis, cardiovascular, gastrointestinal, endocrine or neurodegenerative diseases, or certain cancers in which $(Ca^{2+})_e$ ions are abnormally high.

Secondary hyperparathyroidism is observed during chronic renal insufficiency and is characterized by hyperplasia of the parathyroid glands and an increase in circulating PTH. Renal insufficiency is also accompanied by renal osteodystrophy which is characterized by bone disorders with a high or low renewal of the bone mass (osteitis fibrosa, osteomalacia).

Osteoporosis is a multifactorial disease which depends in particular on the age and the gender. While menopausal women are very highly affected, osteoporosis is found increasingly to be a problem in old men, and there are currently no truly satisfactory treatments. Its social cost could increase further in the coming years, particularly in our European society where the lifespan is increasing. Osteoporosis is currently treated with estrogens, calcitonin or biphosphonates which prevent bone resorption without stimulating new bone growth. More recent data demonstrate that intermittent increases in PTH or its derivatives are effective in the treatment of osteoporosis and make it possible to remodel the bone by stimulating bone formation (Whitfield et al., R. G. Landes Co., Austin, USA, 1998). This novel therapeutic route for the treatment of osteoporosis appears very advantageous although major problems are linked to the use of the PTH hormone such as the route of injection, but also the appearance of tumors which have been recently observed during clinical trials in humans. The intermittent secretion of endogenous PTH may be obtained by blocking the calcium receptor with the aid of an antagonist molecule, which is beneficial in the treatment of osteoporosis. The secretion of PTH may be blocked by CaSR agonists. This blocking may be followed by a rapid increase in PTH (rebound effect), which is also beneficial in the treatment of osteoporosis.

Taking into account the important role of calcium homeostasis, numerous CaSR modulators have already been used.

Thus, the company NPS Pharmaceutical has developed two main types of family of organic compounds as CaSR agonists, namely polyamines such as NPS 019 (3), and the arylalkylamines, small size molecules of which the best known representative to date is NPS R-568 (2). The compound NPS R-568 was developed from the structure of Fendiline (1), a potent activator of CaSR of the parathyroid gland.

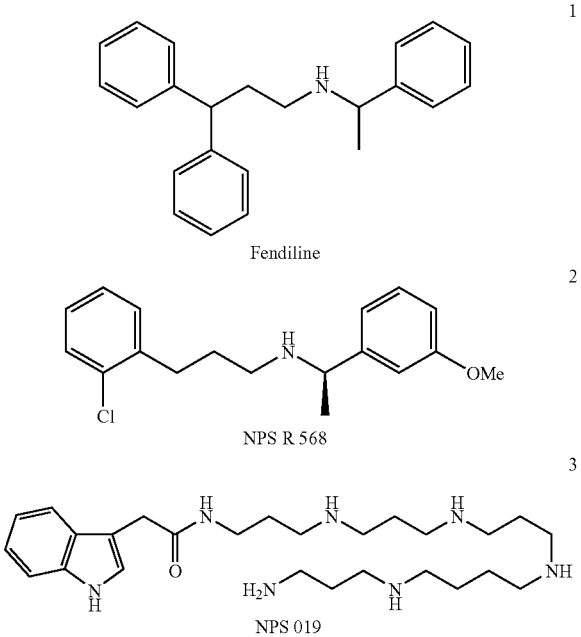

Fendiline

NPS R 568

NPS 019

The compound NPS-R-568 reduces or eliminates osteitis fibrosa in rats (Wada et al., Kidney International, 1998, vol. 53, p. 448–453) and reduces the PTH concentrations in patients (men) suffering from chronic renal insufficiency (Antansen et al., Kidney International, 1998, vol. 53, p. 223–227). This compound was successfully used orally to reduce the concentrations of PTH and of free serum $Ca^{2+}$ ions in menopausal women suffering from primary hyperparathyroidism (Silverberg et al., New Engl. J. Med., 1997, vol. 337, p. 1506–1510). In another study, the compound NPS-R-568 made it possible to reduce between 20–50% the cell proliferation observed in the parathyroid gland in a rat model reproducing chronic renal insufficiency (Wada et al., J. Clin. Invest., 1997, vol. 100, p. 2977–2983). These studies demonstrate that a calcimimetic compound, which is active toward the calcium receptor present on the parathyroid gland, may be considered as an advantageous therapeutic tool for treating certain forms of primary and secondary hyperparathyroidism.

During clinical trials (Phase I–II), the company NPS Pharmaceutical observed a low bioavailability of the compound NPS-R-568 as well as variable clinical effects according to the individuals which could result from polymorphism of the gene encoding CaSR in humans (Nemeth et al., Trends Endoc. Metab, 1999, vol. 10, p. 66–71). Furthermore, during experimental trials in rats, the NPS R-467 compound, (an analog of NPS R-568 (2) in which the chlorine is replaced with a hydrogen) (Nemeth et al., PNAS (USA), 1998, vol. 95, p. 4040–4045) a compound having a structure similar to NPS R-568, proved more selective toward the receptors for the parathyroid compared to those for the thyroid gland. This selectivity can be explained by differences linked to the tissues, which suggests that calcimimetic molecules specific for a tissue may be synthesized and may have considerable clinical importance.

In parallel, the inventors recently reported the preparation and the calcimimetic activity of arylalkyl-1,2-diamines hav-ing the general structure described below (4), and among which the compound PHD 321 (5) constitutes one of the most active products.

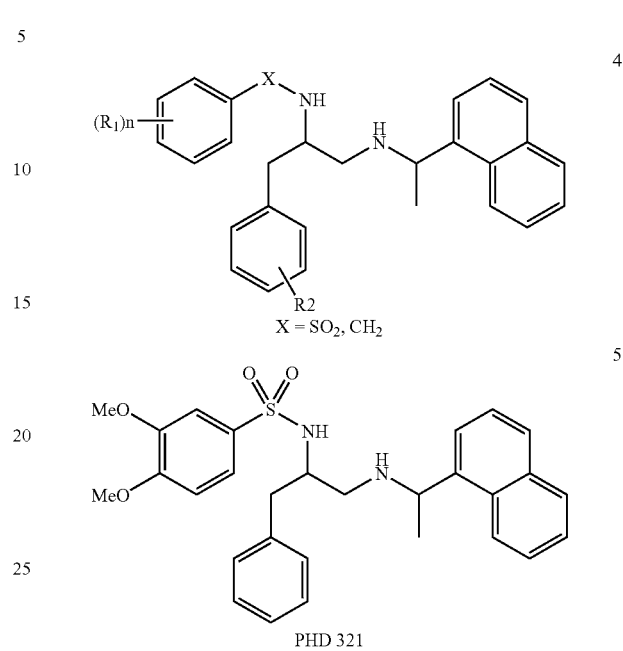

PHD 321

The inventors also recently reported the synthesis of compounds of the following general formula (6):

in which:
X represents a group —NR4, —CH=N— or —CH (R5)—N(R4)—,
Y represents an oxygen or sulfur atom or a group —CR5, —CH(R5), —C(R5)=C(R6)—, —CH(R5)—CH(R6)— or NR provided that when X represents the group —CH=N— or —CH(R5)—N(R4)—, Y represents an oxygen or sulfur atom or the group NR, —C(R5) or —CH(R5),
R represents a hydrogen atom, an alkyl, aryl or aralkyl group,
R1, R5 and R6, which may be identical or different, each represent a hydrogen or halogen atom or an alkyl or alkoxy group,
R2 represents a hydrogen atom or an alkyl group,
R3 represents an aryl group
and R4 represents a hydrogen atom, an alkyl, aryl, aralkyl, alkylsulfonamide, arylsulfonamide or aralkylsulfonamide group.

As regards the CaSR antagonists, the companies SMITH-KLINE BEECHAM and NPS Pharmaceutical have reported in recent patents the preparation of the compounds having the general structure 7 (WO9737967; WO9845255; WO9951241; WO9951569) and of compounds of the pyridinium type (WO9844925). Among these, the most active as calcilytic agents have an IC$_{50}$ of less than $10^{-7}$ M. Such products open new therapeutic windows for the treatment of osteoporosis. However, their arylopropanolamine structure, close to those of β-adrenergics induces an undesirable residual activity at this level.

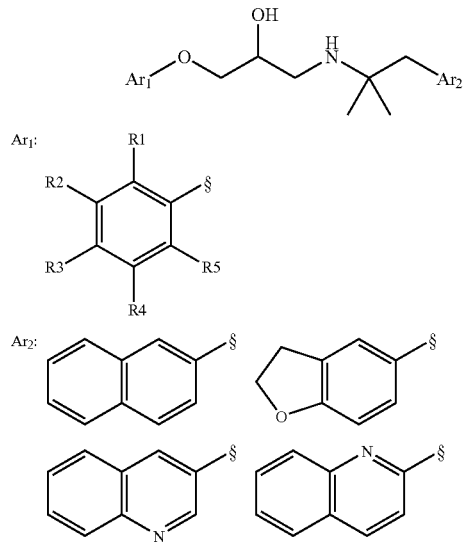

The complete absence of CaSR modulating molecules in clinical medicine and the problems encountered in phase I–II for first-generation calcimimetics underline the need to find novel molecules which modulate CaSR activity.

Consequently, the inventors set themselves the aim of preparing compounds which modulate CaSR activity and which do not possess the abovementioned disadvantages.

The present invention therefore relates to diamines of the following general formula (I):

in which:

A represents a group A1 or A2 of the following general formula:

where R1, R2, R3, R4, R5, R6, R7, R8, R9, R10, R11 and R12, which are identical or different, represent, independently of each other, a hydrogen or halogen atom or an alkyl, cycloalkyl, CN, NO$_2$, hydroxyl, aryl, aralkyl, alkoxy, aryloxy, amino, alkylamino, dialkylamino, cycloalkylamino, arylamino, arylalkylamino, diarylamino, diarylalkylamino, trihaloalkyl or trihaloalkoxy group, provided that in the group A1, at least one of the radicals R1, R2, R3, R4 or R5 represents the hydrogen atom when the other four do not represent the hydrogen atom, B represents a group B1 or B2 of the following general formula:

where R13, R14, R15, R16, R17, R18, R19, R20, R21, R22, R23 and R24, which are identical or different, represent, independently of each other, a hydrogen or halogen atom or an alkyl, cycloalkyl, CN, NO$_2$, hydroxyl, aryl, aralkyl, alkoxy, aryloxy, amino, alkylamino, dialkylamino, cycloalkylamino, arylamino, arylalkylamino, diarylamino, diarylalkylamino, trihaloalkyl or trihaloalkoxy group, provided that in the group B1, at least one of the radicals R13, R14, R15, R16 or R17 represents the hydrogen atom when the other four do not represent the hydrogen atom, X represents an SO$_2$, CH$_2$, C=O or COO group,

Y===Z represents a group of formula CH(R25)—CH(R26) or CH(R27)=CH(R28) where the groups —R25, R26, R27 and R28, which are identical or different, represent, independently of each other, a hydrogen or halogen atom or an alkyl, cycloalkyl, CN, NO$_2$, hydroxyl, aryl, aralkyl, alkoxy, aryloxy, amino, alkylamino, dialkylamino, cycloalkylamino, arylamino, arylalkylamino, diarylamino, diarylalkylamino, trihaloalkyl or trihaloalkoxy group, and their salts with a pharmaceutically acceptable acid, in the form of a racemic mixture or of their optically pure isomers.

Advantageously, A represents the group A1, B represents the group B2 and $$Y=Z$$

represents the group CH(R25)—CH(R26) where R25 and R26 each represent a hydrogen atom.

Still more advantageously, X represents the SO$_2$ group.

Particular examples of diamines according to the present invention are those chosen from the group consisting of the diamines of formulae (Ia) to (Id):

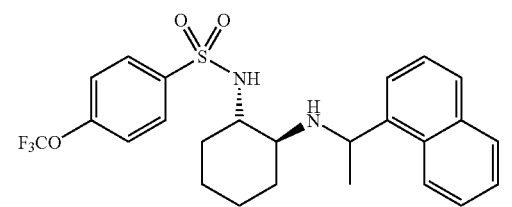

Ia

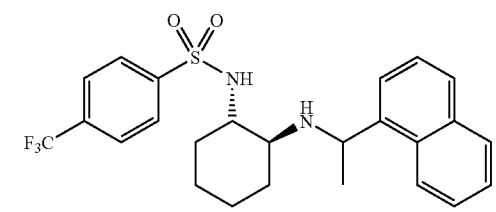

Ib

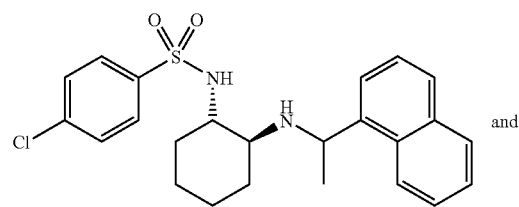

Ic and

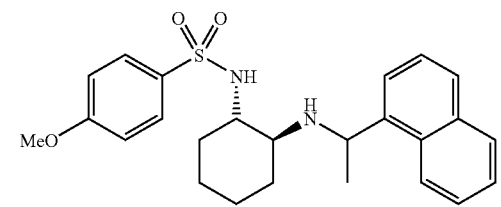

Id and their salts with a pharmaceutically acceptable acid.

The term "pharmaceutically acceptable acid" is understood to mean, for the purposes of the present invention; any nontoxic acid, including organic and inorganic acids. Such acids include acetic, benzenesulfonic, benzoic, citric, ethanesulfonic, fumaric, gluconic, glutamic, hydrobromic, hydrochloric, lactic, maleic, malic, mandelic, methanesulfonic, mucic, nitric, pamoic, pantothenic, phosphoric, succinic, sulfuric, tartaric and para-toluenesulfonic acids. Hydrochloric acid is particularly preferred.

The term "alkyl group" is understood to mean, for the purposes of the present invention, any substituted or unsubstituted, linear or branched $C_1$–$C_6$ alkyl group, in particular the methyl group.

The term "cycloalkyl group" is understood to mean, for the purposes of the present invention, any substituted or unsubstituted, linear or branched $C_3$–$C_6$ cycloalkyl group.

The term "alkoxy group" is understood to mean, for the purposes of the present invention, any alkoxy group of 1 to 6 carbon atoms, which are linear or branched, substituted or unsubstituted, in particular the —OMe group.

The term "aryl group" is understood to mean, for the purposes of the present invention, one or more aromatic rings having 5 to 8 carbon atoms, which may be joined or fused, it being possible for said rings to be substituted. In particular, the aryl groups may be phenyl or naphthyl groups.

The term "aralkyl group" is understood to mean, for the purposes of the present invention, any aryl group as defined above, linked via an alkyl group as defined above. In particular, an aralkyl group is a benzyl or naphthylmethyl group.

The term "aryloxy group" is understood to mean, for the purposes of the present invention, any aryl group as defined above, linked to an oxygen atom.

The term "alkylamino" is understood to mean, for the purposes of the present invention, any amine group substituted with a single alkyl group as defined above.

The term "dialkylamino" is understood to mean, for the purposes of the present invention, any amine group substituted with two alkyl groups, which are identical or different, as defined above.

The term "cycloalkylamino" is understood to mean, for the purposes of the present invention any amine group in which the two substituents are linked to each other to form a $C_2$–$C_6$ cyclic aliphatic chain.

The term "arylamino" is understood to mean, for the purposes of the present invention, any amine group substituted with a single aryl group as defined above.

The term "arylalkylamino" is understood to mean, for the purposes of the present invention, any amine group substituted with a single arylalkyl group as defined above.

The term "diarylamino" is understood to mean, for the purposes of the present invention, any amine group substituted with two aryl groups, which are identical or different, as defined above.

The term "diarylalkylamino" is understood to mean, for the purposes of the present invention, any amine group substituted with two aralkyl groups, which are identical or different, as defined above.

The term "trihaloalkyl" is understood to mean, for the purposes of the present invention, any alkyl group as defined above, substituted with three halogen atoms.

The term "trihaloalkoxy" is understood to mean, for the purposes of the present invention, any alkoxy group as defined above, substituted with three halogen atoms.

Preferred examples of a halogen atom are Cl and F.

The compounds according to the invention all have an asymmetric carbon and can therefore exist in the form of optical isomers. The present invention comprises these isomers pure or as a mixture.

The present invention also relates to the method of preparing these compounds.

The preparation of the molecules may be simply carried out in 4 or 5 stages depending on $$Y \text{---} Z$$

of the general formula I. In all cases, the first two stages are the following:

a) reaction, advantageously in the presence of $Cu^{I\ or\ II}$, between an olefin of general formula VI:

VI in which:

$$Y \text{---} Z$$

represents the group $CH_2$—$CH_2$ or the group $CH(R27)$=$CH(R28)$ where R27 and R28 are as defined in formula I, and the compound of formula VII:

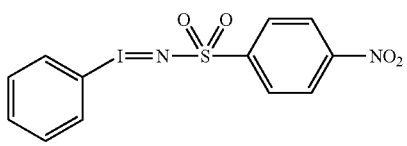

VII to give the aziridine of general formula IV:

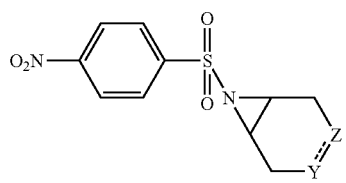

IV in which $$Y \text{---} Z$$

represents the group $CH_2$—$CH_2$ or the group $CH(R27)$=$CH(R28)$ where R27 and R28 are as defined in formula I, b) nucleophilic opening of the aziridine of general formula IV by the compound of the following general formula V:

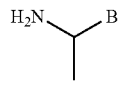

V in which B is as defined in formula I, to give the diamine of general formula III

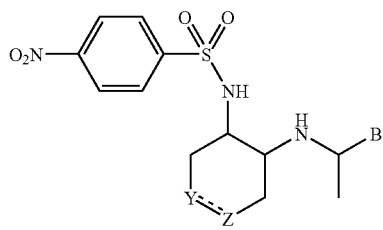

III in which:

$$Y \text{---} Z$$

represents the group $CH_2$—$CH_2$ or the group $CH(R27)$=$CH(R28)$ and

B, R27 and R28 are as defined in formula I.

These two stages are carried out by methods well known to persons skilled in the art. The following stages depend on the type of radical X desired.

To obtain the diamines of general formula I in which X represents the $CH_2$, C=O or COO group, respectively, and $$Y \text{---} Z$$

represents the group $CH_2$—$CH_2$ or the group $CH(R27)$=$CH(R28)$, method a)b) comprises, in addition, the following stages:

$c_1$) selective introduction of an arylmethyl, aroyl or aryloxycarbonyl group, respectively, depending on the radical X which it is desired to introduce, said groups being optionally substituted, into the compound of formula III, and $d_1$) deprotection of the compound obtained.

Stages $c_1$) and $d_1$) are carried out by methods well known to persons skilled in the art.

To obtain the diamines of general formula I in which X represents respectively the $SO_2$ group and $$Y \text{---} Z$$

represents the group $CH_2$—$CH_2$ or the group $CH(R27)$=$CH(R28)$, method a)b) comprises, in addition, the following stages:

$c_2$) the compound of formula III undergoes a deprotection reaction, and d$_2$) an optionally substituted arylsulfonyl group is introduced into the NH$_2$ functional group of the compound thus obtained.

Stages c$_2$) and d$_2$) are carried out by methods well known to persons skilled in the art.

To obtain the diamines of general formula I in which

represents the group CH(R25)—CH(R26) where at least one of the radicals R25 and R26 does not represent the hydrogen atom, the method comprises, in addition, either after stage d$_1$), or after stage d$_2$), depending on the radical X desired, a final stage consisting in the selective introduction of the R25 and R26 radical(s) which do not represent the hydrogen atom into the molecule of the following general formula II:

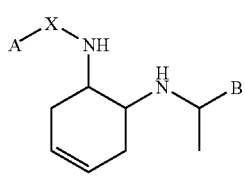

in which:

A, B and X are as defined in formula I.

The introduction of the R25 and/or R26 radical(s) may be carried out by methods well known to persons skilled in the art depending on the type of radical desired, in particular by epoxidation, aziridination, dihydroxylation, aminohydroxylation or Heck reaction.

The olefins of general formula VI and the compound of general formula V are easily commercially available. The compound of formula VII may be easily produced according to the method described by Evans et al. in *Journal of the American Society*, 1994, vol. 116, p. 2742.

The simplicity of the method of preparation of the compounds of formula I as described above and its very good yield make it possible to introduce a large variety of substituents R1 to R28.

The present invention also relates to pharmaceutical compositions comprising, as active ingredient, at least one of the diamines according to the present invention and an appropriate excipient. Such compositions may also comprise other active ingredients. These compositions may be formulated for administration to mammals, including humans. The dosage varies according to the treatment and according to the condition in question. These compositions are prepared so as to be administrable by the digestive or parenteral route.

In the pharmaceutical compositions of the present invention for oral, sublingual, subcutaneous, intramuscular, intravenous, transdermal, local or rectal administration, the active ingredient may be administered in unit forms for administration, mixed with conventional pharmaceutical carriers, to animals or to human beings. The appropriate unit forms for administration comprise the forms for administration by the oral route such as tablets, gelatin capsules, powders, granules and oral solutions or suspensions, the forms for sublingual and buccal administration, the forms for subcutaneous, intramuscular, intravenous, intranasal or intraocular administration and the forms for rectal administration.

When a solid composition is prepared in the form of tablets, the main active ingredient is mixed with a pharmaceutical vehicle such as gelatin, starch, lactose, magnesium stearate, talc, gum arabic and the like. It is possible to coat the tablets with sucrose or other appropriate materials or it is possible to treat them such that they have a prolonged or delayed activity and they continuously release a predetermined quantity of active ingredient.

A preparation in gelatin capsules is obtained by mixing the active ingredient with a diluent and by pouring the mixture obtained into soft or hard gelatin capsules.

A preparation in syrup or elixir form may contain the active ingredient together with a sweetener, an antiseptic, as well as a taste enhancer and an appropriate coloring agent.

The water-dispersible powders or granules may contain the active ingredient mixed with dispersing agents or wetting agents, or suspending agents, and with flavor correctors or sweeteners.

For rectal administration, suppositories are used which are prepared with binders which melt at rectal temperature, for example cocoa butter or polyethylene glycols.

For parenteral, intranasal or intraocular administration, aqueous suspensions, isotonic saline solutions or sterile and injectable solutions which contain pharmacologically acceptable dispersing agents and/or wetting agents are used.

The active ingredient may also be formulated in the form of microcapsules, optionally with one or more carrier additives.

The present invention also relates to the use of these diamines and of the pharmaceutical compositions containing them as modulator of CaSR activity.

Advantageously, the diamines according to the invention, for which X represents the SO$_2$, C=O or COO group, may be used as CaSR antagonists and those for which the group X represents the CH$_2$ group as CaSR agonists.

CaSRs can in particular be found in the parathyroid gland, the thyroid, the bone cells, sensitive neurones, the stomach, the lungs, the kidney, the pituitary gland, the brain, the hypothalamus, the olfactory surfaces or the hippocampus.

The diamines according to the invention and the pharmaceutical compositions comprising them can be used as a medicament, in particular for the treatment of physiological diseases or disorders linked to disturbances in the CaSR activity.

Still more particularly, in the case of the diamines for which X represents the SO$_2$, C=O or COO group, these physiological diseases or disorders are of the type including demyelinating diseases associated with the expression of CaSRs in the oligodendrocytes, osteoporosis, Paget's disease, rheumatoid arthritis, tumors associated with humoral hypercalcemia, osteoarthritis, osteosarcomas, fractures, cardiovascular, gastrointestinal, endocrin or neurodegenerative diseases or cancers where $(Ca^{2+})_e$ ions are abnormally high and in the case of the diamines for which X represents the CH$_2$ group, these physiological diseases or disorders are of the type including diseases linked to hypercalcemia, primary or secondary hyperparathyroidism, osteoporosis, cardiovascular, gastrointestinal, endocrin or neurodegenerative diseases or certain cancers where the $(Ca^{2+})$ e ions are abnormally high. Secondary hyperparathyroidism is more particularly observed during chronic renal insufficiency.

The present invention also relates to the aziridines of general formula IV:

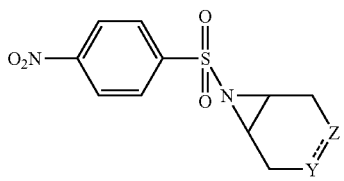

IV in which:

represents the group CHR27=CHR28 where R27 and R28 are as defined in formula I.

The following example of synthesis of a compound according to the invention is given without limitation and illustrates the invention.

Synthesis of N-p-(methoxybenzenesulfonyl)-7-azabicyclo-[4.1.0]heptane

To a solution of copper trifluoromethanesulfonate (56 mg; 0.01 mmol) in 4 ml of acetonitrile distilled over CaCH$_2$, in the presence of an activated molecular sieve, are successively added, at 0° C. under argon, cyclohexene (0.51 ml; 5 mmol) and, in portions over a period of 3 hours, [N-(p-methoxyphenylsulfonyl)imino]-phenyliodinane (Ph1=NSO2Ph-p-MeO) (0.390 g; 1 mmol). The heterogeneous mixture, which is green in color, is stirred at 0° C. for 6 hours before being filtered on silica (eluent: ethyl acetate) in order to remove the molecular sieve and the copper salts. After evaporation of the solvents, the yellow oily residue is purified by chromatography on silica (eluent: heptane/ethyl acetate: 4/1) to give 0.120 g (0.45 mmol; 45%) of an impure white solid.

Mass spectroscopy (Es)=m/z=267 [M+H]$^+$

Synthesis of N1-(4-methoxybenzenesulfonyl)-N-2-[1-(1-naphthyl)ethyl]cyclohexane-1,2-diamine: PHD 263

To a solution of aziridine prepared beforehand (80 mg; 0.30 mmol) in 1 ml of tetrahydrofuran (THF), are successively added triethylamine (0.009 ml; 0.06 mmol) and 1-(1-naphthyl)ethylamine (0.145 ml; 0.90 mmol). After stirring for 3 days at 60° C., the medium is concentrated before being purified on a silica column (eluent: heptane/ethyl acetate: 1/1). 125 mg (0.285 mmol; 95%) of the compound of aziridine opening are isolated in the form of a colorless foam. The diamine is then converted to its hydrochloride by treatment with a solution of HCl in methanol.

Mass spectrometry (ES): m/z: 439 [M+H]$^+$

Melting point: 135–140° C. (decomposition)

The other compounds of Table 1 are prepared in the same manner as PHD 263.

TABLE 1

Structure of various compounds according to the invention

| Reference | Empirical formula<br>Molar mass | Structure |
|---|---|---|
| PHD 263 | C$_{25}$H$_{30}$N$_2$O$_3$S.HCl<br>475.05 | 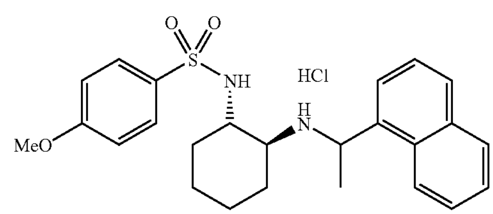 |
| PHD 346 | C$_{25}$H$_{29}$ClN$_2$.2HCl<br>485.89 | 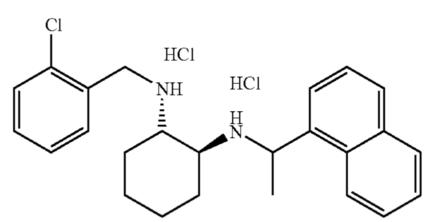 |
| PHD 348 | C$_{25}$H$_{29}$FN$_2$.2HCl<br>449.44 | 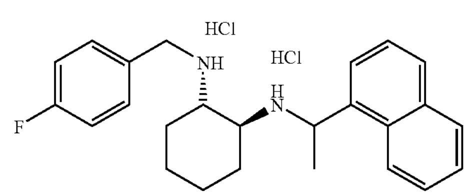 |

TABLE 1-continued

Structure of various compounds according to the invention

| Reference | Empirical formula Molar mass | Structure |
|---|---|---|
| PHD 349 | C$_{26}$H$_{32}$N$_2$O$_4$S.HCl 505.08 | 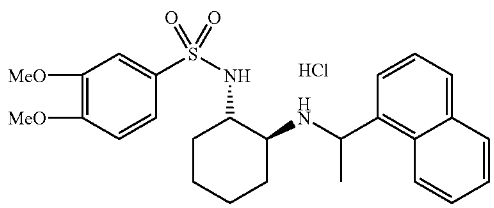 |
| PHD 350 | C$_{24}$H$_{27}$ClN$_2$O$_3$S.HCl 479.47 | 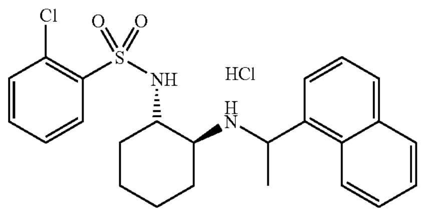 |
| PHD 397 | C$_{24}$H$_{27}$N$_3$O$_4$S 453.57 | 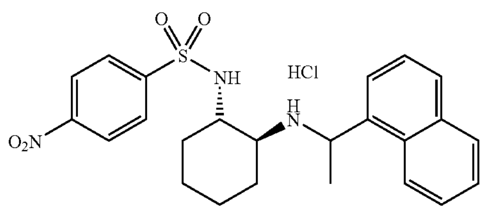 |
| PHD 401 | C$_{25}$H$_{27}$F$_3$N$_2$O$_3$S.HCl 529.03 | 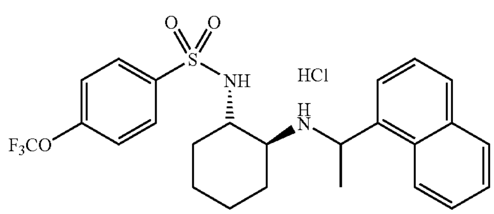 |
| PHD 403 | C$_{25}$H$_{27}$F$_3$N$_2$O$_2$S.HCl 513.03 | 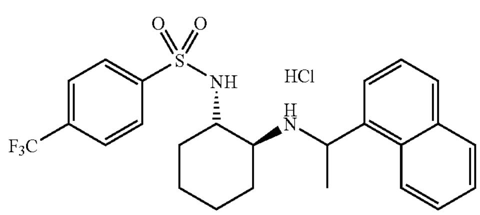 |
| PHD 404 | C$_{28}$H$_{30}$N$_2$O$_2$S 458.63 | 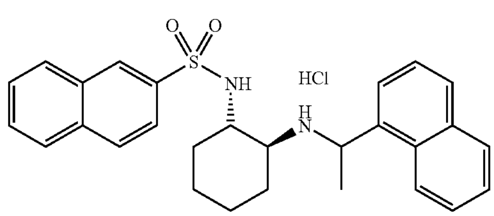 |
| PHD 406 | C$_{24}$H$_{27}$ClN$_2$O$_2$S.HCl 479.47 | 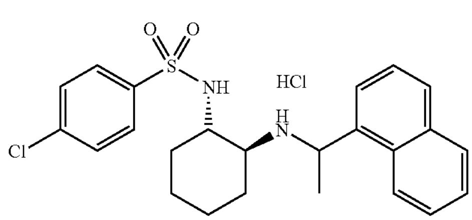 |

TABLE 1-continued

Structure of various compounds according to the invention

| Reference | Empirical formula Molar mass | Structure |
|---|---|---|
| PHD 408 | $C_{24}H_{28}N_2O_2S \cdot HCl$ 445.02 | 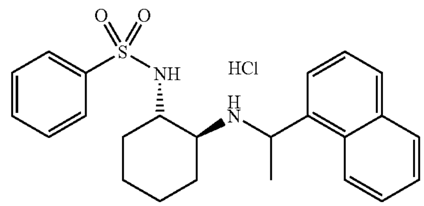 |
| PHD 511 | $C_{25}H_{26}N_2O_3S \cdot HCl$ 473.04 | 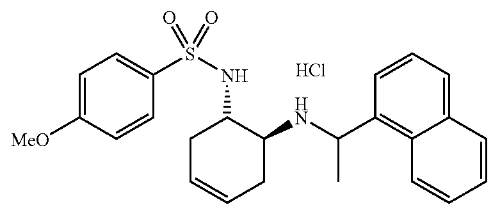 |
| AK 115 | $C_{26}H_{32}N_2O_4S \cdot HCl$ 505.08 | 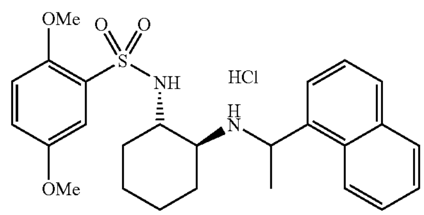 |
| AK 116 | $C_{24}H_{27}N_2O_2SCl \cdot HCl$ 479.47 | 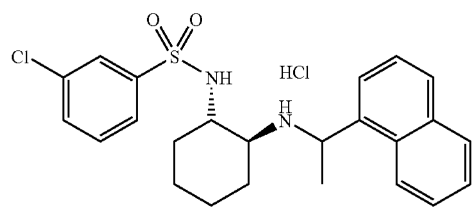 |
| AK 117 | $C_{24}H_{25}N_2O_2SCl_3 \cdot HCl$ 548.35 | 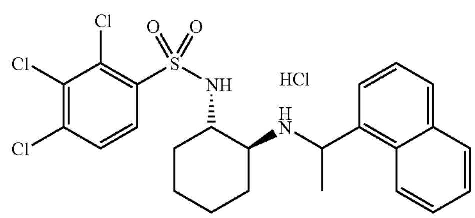 |

Activity on Transfected Cells Expressing the Receptor Sensitive to Extracellular Calcium $(Ca^{2+})_e$ Ions 1. Procedure The calcilytic or calcimimetic activity of compounds according to the invention was estimated by measuring the inhibition of the accumulation of tritiated inositol phosphates induced by 9 mM extracellular calcium ions in the presence of 10 µM of each of the compounds in CHO(CaS) cells. The technique for measuring the accumulation of tritiated inositol phosphates [$^3$H]IP which is used is that described in Ruat et al., *J. Biol. Chem.*, 1996, vol. 271, p. 5972-5975. Only the mode of incubating the compounds is modified. After a preincubation of 15 min of the compounds according to the invention in the presence of a basal concentration of $(Ca^{2+})_e$ equal to 2 mM, the compounds are incubated for 30 min in the presence of a $(Ca^{2+})_e$ concentration of 4 or 9 mM. The results, mean of 2 to 4 independent experiments each carried out in triplicate, are grouped together in Table 2.

2. Result

The activity of the compounds is expressed as a percentage of the control activity measured in the presence of $(Ca^{2+})_e$ alone of concentration 4 mM or 9 mM.

The compound PHD 350 leads to a 25% inhibition of the accumulation of [$^3$H]IP induced by 9 mM $(Ca^{2+})$ et PHD 401 leads to an 82% inhibition under the same conditions and the compound PHD 263, for its part, inhibits the same response by 64%.

By contrast, the compounds PHD 346 and PHD 348 exhibit a calcimimetic activity since they activate the production of [$^3$H]IP.

TABLE 2

Antagonist or agonist activity of the compounds according to the invention on the accumulation of tritiated inositol phosphates [$^3$H]IP which is induced by 9 mM $Ca^{2+}$.

| Compounds at 10 μM | Accumulation of [$^3$H]IP % relative to the control |
|---|---|
| Control | 100 |
| PHD 346 | 110 ± 6 |
| PHD 348 | 119 ± 12 |
| PHD 350 | 74 ± 2 |
| PHD 349 | 64 ± 5 |
| PHD 408 | 56 ± 4 |
| PHD 397 | 43 ± 1 |
| PHD 404 | 39 ± 7 |
| PHD 263 | 37 ± 5 |
| PHD 406 | 28 ± 1 |
| PHD 403 | 21 ± 1 |
| PHD 401 | 18 ± 3 |
| PHD 511 | 75 ± 10 |
| AK 115 | 100 ± 4 |
| AK 116 | 40 ± 5 |
| AK 117 | 42 ± 5 |

Specificity of the Activity of the Molecules According to the Invention

To assess the specificity of the antagonist activity of the molecules according to the invention, the effect of one of them, PHD 263, was studied under various calcium conditions, in the presence or otherwise of ATP on CHO(WT*) and CHO(CaSR) cells. The CHO(WT*) cells were transfected with the plasmid alone and do not express CaSR. The accumulation of tritiated inositol phosphates is expressed as a percentage of the basal level observed in the presence of 2 mM $Ca^{2+}$ (100) in the CHO(WT*) or CHO(CaSR) cells.

The molecules according to the invention, used alone at a concentration of 10 μM, such as PHD 263, lead to little or no accumulation of [$^3$H]IP in the control CHO(WT*) cells or the CHO(CaSR) cells (124±10%) which suggests a weak nonspecific activity in these cells independent of the presence of CaSR.

PHD 263 (10 μM) has the same effect on the [$^3$H]IP response in the CHO(WT*) cells in the presence of 2 or 4 mM calcium, indicating an absence of a nonspecific effect of the compound linked to the variation of [$Ca^{2+}$]$_e$. The PHD 263 (10 μM) effect adds to that of ATP in these CHO(WT) cells; it does not therefore inhibit the [$^3$H]IP response induced by another receptor coupled to the phospholipase C pathway.

The invention claimed is:

1. A diamine of general formula (I):

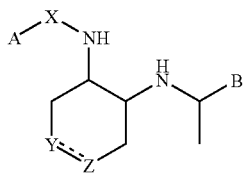

I wherein:

A is A1 or A2 having the following general formula:

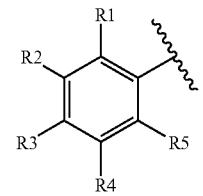

A1

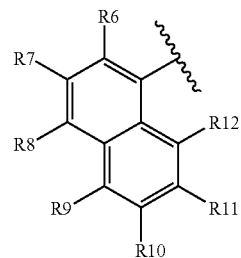

A2 wherein R1, R2, R3, R4, R5, R6, R7, R8, R9, R10, R11 and R12 are independently selected from the group consisting of hydrogen, halogen, alkyl, cycloalkyl, CN, $NO_2$, hydroxyl, aryl, aralkyl, alkoxy, aryloxy, amino, alkylamino, dialkylamino, cycloalkylamino, arylamino, arylalkylamino, diarylamino, diarylalkylamino, trihaloalkyl and trihaloalkoxy, provided that when A is A1 at least one of the radicals R1, R2, R3, R4 or R5 is hydrogen when the other four radicals are not hydrogen, B is B1 or B2 having the following general formula:

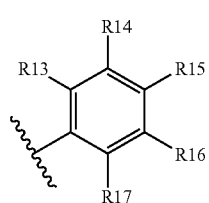

B1

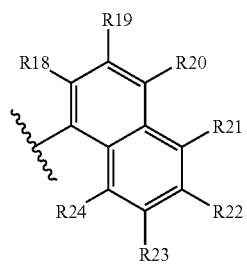

B2 wherein R13, R14, R15, R16, R17, R18, R19, R20, R21, R22, R23 and R24, are independently selected from the group consisting of hydrogen, halogen, alkyl, cycloalkyl, CN, $NO_2$, hydroxyl, aryl, aralkyl, alkoxy, aryloxy, amino, alkylamino, dialkylamino, cycloalkylamino, arylamino, arylalkylamino, diarylamino, diarylalkylamino, trihaloalkyl and trihaloalkoxy, provided that when B is B1, at least one of the radicals R13, R14, R15, R16 or R17 is hydrogen when the other four radicals are not hydrogen, X is SO₂, CH₂, C=O or COO, $$Y\text{---}Z$$

is CH(R25)—CH(R26) or CH(R27)=CH(R28), wherein R25, R26, R27 and R28 are independently selected from the group consisting of hydrogen, halogen, alkyl, cycloalkyl, CN, NO₂, hydroxyl, aryl, aralkyl, alkoxy, aryloxy, amino, alkylamino, dialkylamino, cycloalkylamino, arylamino, arylalkylamino, diarylamino, diarylalkylamino, trihaloalkyl and trihaloalkoxy; and salts thereof optionally further comprising a pharmaceutically acceptable acid, wherein the diamine is a racemic mixture of isomers or a purified isomer.

2. The diamine of claim 1, wherein A is A1, B is B2 and $$Y\text{---}Z$$

is CH(R25)—CH(R26), wherein R25 and R26 are both hydrogen.

3. The diamine of claim 1, wherein X is SO₂.

4. The diamine of claim 1, wherein the diamine is selected from the group consisting of the following formulae:

Ia
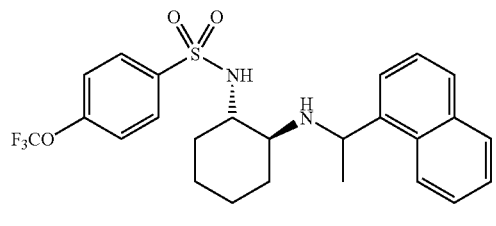

Ib
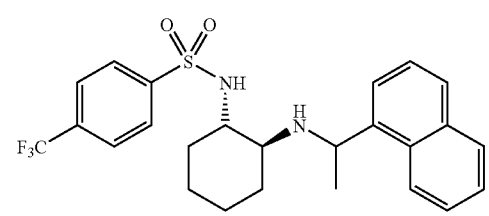

Ic
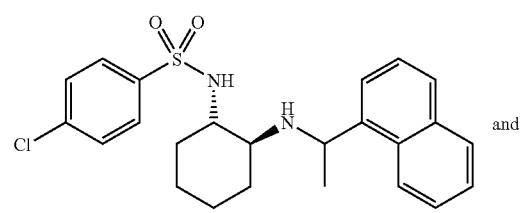

and

Id
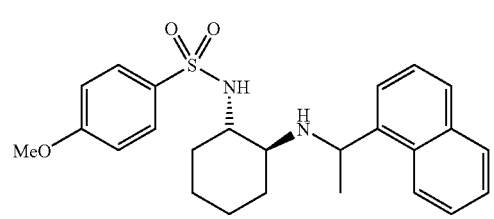

and the salts thereof further comprising a pharmaceutically acceptable acid.

5. A method for preparing the diamine of claim 1, wherein $$Y\text{---}Z$$

is CH(R25)—CH(R26) and at least one of the radicals R25 and R26 is not hydrogen, wherein at least one of the radical(s) R25 and R26 is selectively introduced into the molecule to yield the following general formula II:

II
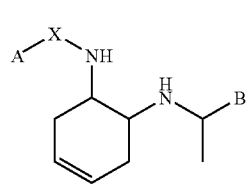

A is A1 or A2 having the following general formula:

A1
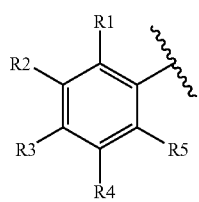

A2
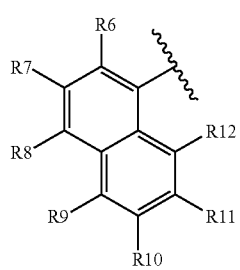

wherein R1, R2, R3, R4, R5, R6, R7, R8, R9, R10, R11 and R12 are independently selected from the group consisting of hydrogen, halogen, alkyl, cycloalkyl, CN, NO₂, hydroxyl, aryl, aralkyl, alkoxy, aryloxy, amino, alkylamino, dialkylamino, cycloalkylamino, arylamino, arylalkylamino, diarylamino, diarylalkylamino, trihaloalkyl and trihaloalkoxy, provided that when A is A1 at least one of the radicals R1, R2, R3, R4 or R5 is hydrogen when the other four radicals are not hydrogen, B is B1 or B2 having the following geral formula:

B1
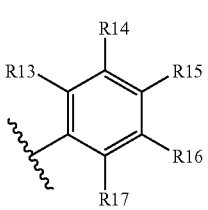

-continued

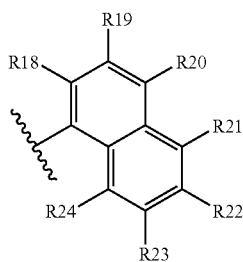

B2 wherein R13, R14, R15, R16, R17, R18, R19, R20, R21, R22, R23 and R24, are independently selected from the group consisting of hydrogen, halogen, alkyl, cycloalkyl, CN, NO$_2$, hydroxyl, aryl, aralkyl, alkoxy, aryloxy, amino, alkylamino, dialkylamino, cycloalkylamino, arylamino, arylalkylamino, diarylamino, diarylalkylamino, trihaloalkyl and trihaloalkoxy, provided that when B is B1, at least one of the radicals R13, R14, R15, R16 or R17 is hydrogen when the other four radicals are not hydrogen, and X is SO$_2$, CH$_2$, C=O or COO.

6. A method for preparing the diamine of claim 1, wherein $$Y=\!=\!=Z$$

is CH$_2$–CH$_2$ or CH(R27)=CH(R28) and X is CH$_2$, C=O or COO comprising the steps of:

a) selectively introducing an arylmethyl, aroyl or aryloxycarbonyl group, said groups being optionally substituted, to generate the compound depicted in formula III:

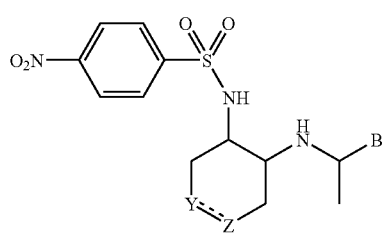

III wherein B is B1 or B2 having the following general formula:

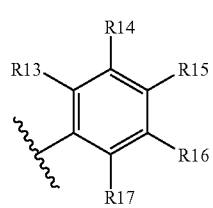

B1

-continued

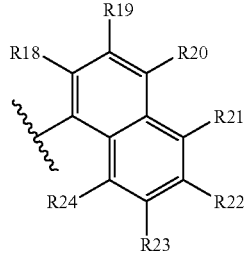

B2 wherein R13, R14, R15, R16, R17, R18, R19, R20, R21, R22, R23 and R24, are independently selected from the group consisting of hydrogen, halogen, alkyl, cycloalkyl, CN, NO$_2$, hydroxyl, aryl, aralkyl, alkoxy, aryloxy, amino, alkylamino, dialkylamino, cycloalkylamino, arylamino, arylalkylamino, diarylamino, diarylalkylamino, trihaloalkyl and trihaloalkoxy, provided that when B is B1, at least one of the radicals R13, R14, R15, R16 or R17 is hydrogen when the other four radicals are not hydrogen, and R27 and R28 are independently selected from the group consisting of hydrogen, halogen, alkyl, cycloalkyl, CN, NO$_2$, hydroxyl, aryl, aralkyl, alkoxy, aryloxy, amino, alkylamino, dialkylamino, cycloalkylamino, arylamino, arylalkylamino, diarylamino, diarylalkylamino, trihaloalkyl and trihaloalkoxy; and b) deprotecting the compound obtained in step (a).

7. A method for preparing the diamine of claim 1, wherein X is SO$_2$ and $$Y=\!=\!=Z$$

is CH$_2$–CH$_2$ or CH(R27)=CH(R28), comprising the steps of:

a) subjecting a compound of formula III

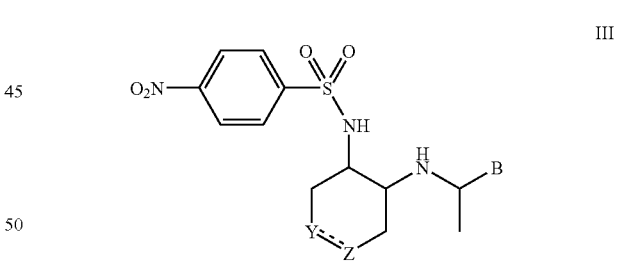

III wherein B is B1 or B2 having the following general formula:

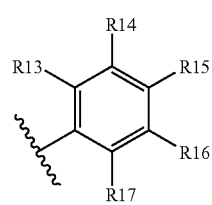

B1

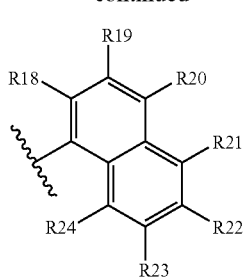

wherein R13, R14, R15, R16, R17, R18, R19, R20, R21, R22, R23 and R24, are independently selected from the group consisting of hydrogen, halogen, alkyl, cycloalkyl, CN, NO2, hydroxyl, aryl, aralkyl, alkoxy, aryloxy, amino, alkylamino, dialkylamino, cycloalkylamino, arylamino, arylalkylamino, diarylamino, diarylalkylamino, trihaloalkyl and trihaloalkoxy, provided that when B is B1, at least one of the radicals R13, R14, R15, R16 or R17 is hydrogen when the other four radicals are not hydrogen, and R27 and R28 are independently selected from the group consisting of hydrogen, halogen, alkyl, cycloalkyl, CN, NO$_2$, hydroxyl, aryl, aralkyl, alkoxy, aryloxy, amino, alkylamino, dialkylamino, cycloalkylamino, arylamino, arylalkylamino, diarylamino, diarylalkylamino, trihaloalkyl and trihaloalkoxy; and to a deprotection reaction, and b) introducing an optionally substituted arylsulfonyl group into the NH$_2$ functional group of the compound obtained in step (a).

8. The method of claim 5, wherein X is CH$_2$, C=O or COO and the compound of formula II is prepared by the method of claim 6.

9. The method of claim 5 wherein X is SO$_2$, and the compound of formula II is prepared by the method of claim 7.

10. The method of claim 6, wherein the compound of formula III is prepared by the step of nucleophilic opening of an aziridine of general formula IV:

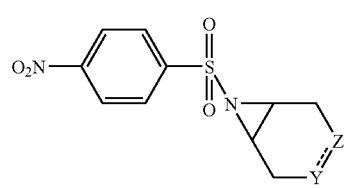

wherein

Y═Z is CH$_2$–CH$_2$ or CH(R27)═CH(R28), wherein R27 and R28 are independently selected from the group consisting of hydrogen, halogen, alkyl, cycloalkyl, CN, NO$_2$, hydroxyl, aryl, aralkyl, alkoxy, aryloxy, amino, alkylamino, dialkylamino, cycloalkylamino, arylamino, arylalkylamino, diarylamino, diarylalkylamino, trihaloalkyl and trihaloalkoxy, said nucleophilic opening being performed by a compound having the following general formula V:

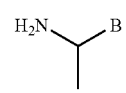

wherein B is B1 or B2 having the following general formula:

wherein R13, R14, R15, R16, R17, R18, R19, R20, R21, R22, R23 and R24 are independently selected from the group consisting of hydrogen, halogen, alkyl, cycloalkyl, CN, NO$_2$, hydroxyl, aryl, aralkyl, alkoxy, aryloxy, amino, alkylamino, dialkylamino, cycloalkylamino, arylamino, arylalkylamino, diarylamino, diarylalkylamino, trihaloalkyl and trihaloalkoxy, provided that in the group B1, at least one of the radicals R13, R14, R15, R16 or R17 represents the hydrogen atom when the other four radicals do not represent hydrogen.

11. The method of claim 10, wherein the compound of formula IV is prepared by reaction between an olefin of general formula VI:

VI wherein

Y═Z is CH$_2$–CH$_2$ or CH(R27)═CH(R28) and a compound having the following formula VII:

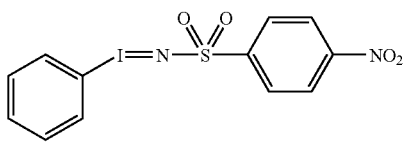

VII wherein I is iodine.

12. A pharmaceutical composition comprising at least one diamine of claim 1 and an appropriate pharmaceutical excipient.

13. A method of treating osteoporosis, or cardiovascular diseases comprising administration of an effective amount of the diamine of claim 1, wherein X is $SO_2$, C=O or COO.

14. A method of treating primary or secondary hyperparathyroidism, osteoporosis or cardiovascular diseases comprising administration of an effective amount of the diamine of claim 1, wherein X is $CH_2$.

15. An aziridine of general formula IV:

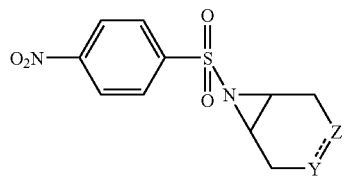

IV wherein

Y═══Z is CH(R27)═CH(R28), and wherein R27 and R28 are independently selected from the group consisting of hydrogen, halogen, alkyl, cycloalkyl, CN, $NO_2$, hydroxyl, aryl, aralkyl, alkoxy, aryloxy, amino, alkylamino, dialkylamino, cycloalkylamino, arylamino, arylalkylamino, diarylamino, diarylalkylamino, trihaloalkyl and trihaloalkoxy.

* * * * *